US009626943B1

(12) United States Patent
Hughlett (10) Patent No.: US 9,626,943 B1
(45) Date of Patent: Apr. 18, 2017

(54) METHOD AND APPARATUS FOR PRODUCING BALANCED DRUMSTICK PAIRS

(71) Applicant: David James Hughlett, Oconomowoc, WI (US)

(72) Inventor: David James Hughlett, Oconomowoc, WI (US)

(*) Notice: Subject to any disclaimer, the term of this patent is extended or adjusted under 35 U.S.C. 154(b) by 373 days.

(21) Appl. No.: 14/189,445

(22) Filed: Feb. 25, 2014

Related U.S. Application Data

(63) Continuation-in-part of application No. 12/807,367, filed on Sep. 3, 2010, now Pat. No. 8,977,515.

(60) Provisional application No. 61/768,673, filed on Feb. 25, 2013, provisional application No. 61/335,402, filed on Jan. 7, 2010.

(51) Int. Cl.
| | |
|---|---|
| *G01N 9/36* | (2006.01) |
| *G10D 13/00* | (2006.01) |
| *G01B 5/02* | (2006.01) |
| *G01B 5/14* | (2006.01) |
| *G01G 9/00* | (2006.01) |

(52) U.S. Cl.
CPC ............ *G10D 13/003* (2013.01); *G01B 5/02* (2013.01); *G01B 5/14* (2013.01); *G01G 9/00* (2013.01); *G01N 9/36* (2013.01)

(58) Field of Classification Search
CPC .......... G01B 5/02; G10D 13/003; G01M 1/12
See application file for complete search history.

(56) References Cited

U.S. PATENT DOCUMENTS

| | | | |
|---|---|---|---|
| 1,484,777 A | 2/1924 | Hassenpfug |
| 1,739,275 A | 12/1929 | Zipperstein |
| 2,521,336 A | 9/1950 | Branson |
| 2,735,291 A | 2/1956 | Quinn |
| 3,146,659 A | 9/1964 | Robba et al. |
| 3,147,660 A | 9/1964 | Brilhart |
| 3,165,964 A | 1/1965 | Stys et al. |
| 3,301,119 A | 1/1967 | Gilbert |
| 3,489,052 A | 1/1970 | Colyer et al. |
| 3,958,485 A | 5/1976 | Peters |
| 4,385,544 A | 5/1983 | Heiskell |

(Continued)

OTHER PUBLICATIONS

Pagano, Christopher C., "Dynamic Touch in Varying Media and for Proprioception," Proceedings of the Human Factors and Ergonomics Society 48th Annual Meeting—2004, pp. 1321-1325.

(Continued)

*Primary Examiner* — Mischita Henson
*Assistant Examiner* — Stephanie Bloss
(74) *Attorney, Agent, or Firm* — Young Basile Hanlon & MacFarlane, P.C.

(57) ABSTRACT

One or more drumsticks may be optimally balanced using a grip point of the drumstick by calculating a radius of gyration. The radius of gyration is a controlling parameter wherein the radius of gyration correlates with the grip point, which is itself based on a particular gripping style and hand size. Given the radius of gyration, the center of gravity of the one or more drumsticks may be re-located at a point along the drumstick closely aligned to the radius of gyration. The re-location may be performed by adding a weight to the butt end of the drumstick. Balanced drumstick pairs provide optimum performance, control and handling characteristics for a drummer.

20 Claims, 8 Drawing Sheets

(56) References Cited

U.S. PATENT DOCUMENTS

| | | | |
|---|---|---|---|
| 4,557,176 A | | 12/1985 | Boturia |
| 4,763,557 A | | 8/1988 | Donohue |
| 4,905,566 A | * | 3/1990 | Hughlett ............... G10D 13/003 84/422.4 |
| 5,218,152 A | | 6/1993 | Campbell et al. |
| D362,864 S | | 10/1995 | Berardi |
| 6,028,260 A | * | 2/2000 | LaLonde .............. G10D 13/003 84/422.4 |
| 6,028,261 A | | 2/2000 | Johnson |
| 6,271,451 B1 | | 8/2001 | Gress |
| 6,307,138 B1 | | 10/2001 | Simpson |
| 6,310,278 B1 | | 10/2001 | Butler |
| 6,326,535 B1 | | 12/2001 | Pokallus |
| 6,365,813 B1 | * | 4/2002 | Gress .................. G10D 13/003 84/422.4 |
| 6,759,583 B2 | | 7/2004 | Mizuno et al. |
| 6,924,423 B2 | | 8/2005 | O'Donnell |
| 7,173,176 B2 | | 2/2007 | Nybye |
| 7,439,435 B1 | | 10/2008 | Jendrisak |
| 7,538,264 B1 | | 5/2009 | Turos |
| 7,557,286 B2 | | 7/2009 | Capotosto |
| 2003/0040376 A1 | | 2/2003 | Cackett et al. |
| 2006/0090629 A1 | * | 5/2006 | Nybye ................. G10D 13/003 84/422.4 |
| 2009/0111596 A1 | | 4/2009 | Owen et al. |
| 2011/0162511 A1 | | 7/2011 | Richard |
| 2011/0166820 A1 | | 7/2011 | Hughlett |

OTHER PUBLICATIONS

Hughlett, Dave, "Understanding Drum Techniques," (1985), pp. 1-5, 8-13, 17, 18 and 31.

* cited by examiner

| Grips | L | P | % | CG | NEW CG | % CG |
|---|---|---|---|---|---|---|
| Traditional | 16 | 4.8 | 30.0% | 48.50% | 6.55 | 40.94% |
| | 16 | 5.28 | 35.0% | 48.50% | 6.68 | 41.75% |
| | 16 | 4.8 | 30.0% | 42.50% | 5.76 | 36.00% |
| | 16 | 5.28 | 33.0% | 42.50% | 5.91 | 36.94% |
| | 16 | 6.25 | 39.1% | 48.50% | 6.98 | 43.63% |
| | 16 | 6.25 | 39.1% | 48.50% | 6.98 | 43.63% |
| | 15.5 | 5.43 | 35.0% | 48.00% | 6.38 | 41.16% |
| | 15.5 | 4.65 | 30.0% | 42.50% | 6.16 | 39.74% |
| | 16.5 | 5.43 | 35.0% | 47.00% | 6.66 | 40.36% |
| | 16.5 | 5.77 | 35.0% | 47.00% | 6.78 | 41.09% |
| Corp/Moeller | 16 | 2.0 | 30.0% | 48.50% | 6.80 | 42.50% |
| | 16 | 3.0 | 18.5% | 48.50% | 6.07 | 37.94% |
| | 17 | 4.0 | 23.5% | 48.50% | 7.13 | 41.94% |
| | 17 | 6.25 | 36.8% | 48.50% | 7.25 | 42.65% |
| | 17 | 3.0 | 17.6% | 48.50% | 6.35 | 37.35% |
| Timbale | 16 | 2.0 | 12.5% | 48.50% | 5.80 | 36.25% |
| | 15 | 3.00 | 20.0% | 50.00% | 5.99 | 39.93% |
| max | 17 | 6.25 | 39.1% | 50.00% | 7.25 | 43.6% |
| min | 15 | 2.00 | 12.5% | 42.50% | 5.76 | 36.0% |
| dif | 2 | 4.25 | 26.6% | 7.50% | 1.49 | 7.63% |

METHOD AND APPARATUS FOR PRODUCING BALANCED DRUMSTICK PAIRS

CROSS-REFERENCE TO RELATED PATENT APPLICATIONS

This application claims priority to U.S. Provisional Patent Application No. 61/768,673, filed Feb. 25, 2013, and is a continuation-in-part of U.S. patent application Ser. No. 12/807,367, filed Sep. 3, 2010, which claimed priority to U.S. Provisional Patent Application No. 61/335,402, filed Jan. 7, 2010. The full disclosure of each of these applications is incorporated herein by reference.

FIELD OF THE DISCLOSURE

This disclosure relates in general to drumsticks and in particular to the location of the center of gravity of a drumstick to produce balanced pairs of drumsticks.

BACKGROUND

Drummers have become accustomed to the "feel" of traditional wood drumsticks. The center of gravity, or center of balance, has been determined by the well-known shape of the drumstick having a striking tip mounted on a tapered section and a straight shank and made of a relatively uniform density wood. Investigation shows that this conventional wood drumstick has a center of gravity location limited to 42% to 57.3% of the way from the back or butt end of the drumstick. Taper affects the center of gravity. Further, any single model of drumsticks having the same weight could have a variation in center of gravity location of up to about 3% due to, for example, variations in the wood density.

Wood drumsticks have some less than optimum characteristics in the lack of complete uniformity, lack of durability in use and lack of adequate strength. These deficiencies have given rise to many efforts to improve drumsticks by manufacturing them from metals, plastics, and other materials. Numerous patents have been issued on drumsticks made of these synthetic materials, and in most cases, wood drumsticks have been cited as the desired goal for tonal characteristics and "feel" to the user. That "feel" may be attributable to the center of gravity above.

U.S. Pat. No. 4,905,566 described a drumstick having a weight, preferably a heavy weight such as a lead weight, inserted into a hole at the butt portion of the drumstick that is fixed in place so that the center of gravity of a drumstick was modified to 35% to 41% from the butt end.

BRIEF SUMMARY

In conventional drumsticks, imbalance remains a problem. Inconsistency produces internal forces that limit performance, speed and power—promoting bad techniques that may result in tension and stress and even injury. Earlier efforts to alter the balance of drumsticks often resulted in creating concentrated areas of imbalance detrimental to maneuverability, response and total quality.

The present disclosure considers the fundamental physics of how a drumstick operates in relation to a drummer's grip, its internal forces and the characteristic actions that define the "feel" to the drummer in selecting a center of mass (gravity) position outside the limits of the characteristic center of gravity (e.g., at 42%-50% of the length from the butt end) for conventional wooden drumsticks.

The method, construction and operation of balance correcting a single or plurality of drumsticks generally involves holding constant the radius of gyration for all drumsticks of a particular grip model. In this way, optimum balance correction of drumsticks can be achieved. The drumsticks balanced as described herein turn consistently and allow the drummer to play faster, with more power and yet be more relaxed. They urge the user to rotate his or her hand to a proper orientation that the most power and speed can be delivered with the least effort, desirably reducing injuries.

One method described herein includes calculating a position of an existing center of gravity of a drumstick along a length of the drumstick, the position defining a first axis of rotation perpendicular to a central axis of the drumstick, generating, using the first axis of rotation and a second axis of rotation perpendicular to the central axis of the drumstick, a radius of gyration for the drumstick, the radius of gyration defining a third axis of rotation perpendicular to the central axis of the drumstick and the second axis located at a grip point along the length of the drumstick that is based on a grip technique of a drummer when using the drumstick, and calculating a weight value to change the existing center of gravity to a desired new center of gravity that is based on the radius of gyration.

An apparatus described herein includes a memory and a processor. The processor is configured to execute instructions stored in the memory to calculate a position of an existing center of gravity of a drumstick along a length of the drumstick, the position defining a first axis of rotation perpendicular to a central axis of the drumstick, and generate, using the first axis of rotation and a second axis of rotation perpendicular to the central axis of the drumstick, a radius of gyration for the drumstick, the radius of gyration defining third axis of rotation perpendicular to the central axis of the drumstick and the second axis located at a grip point along the length of the drumstick that is based on a grip technique of a drummer when using the drumstick. Finally, the instructions can cause the processor to calculate a weight value to change the existing center of gravity to a desired new center of gravity that is based on the radius of gyration.

Variations in these and other aspects of this disclosure will be described in additional detail hereafter.

BRIEF DESCRIPTION OF THE DRAWINGS

The description herein makes reference to the accompanying drawings wherein like reference numerals refer to like parts throughout the several views, and wherein.

DETAILED DESCRIPTION

Figure 1:
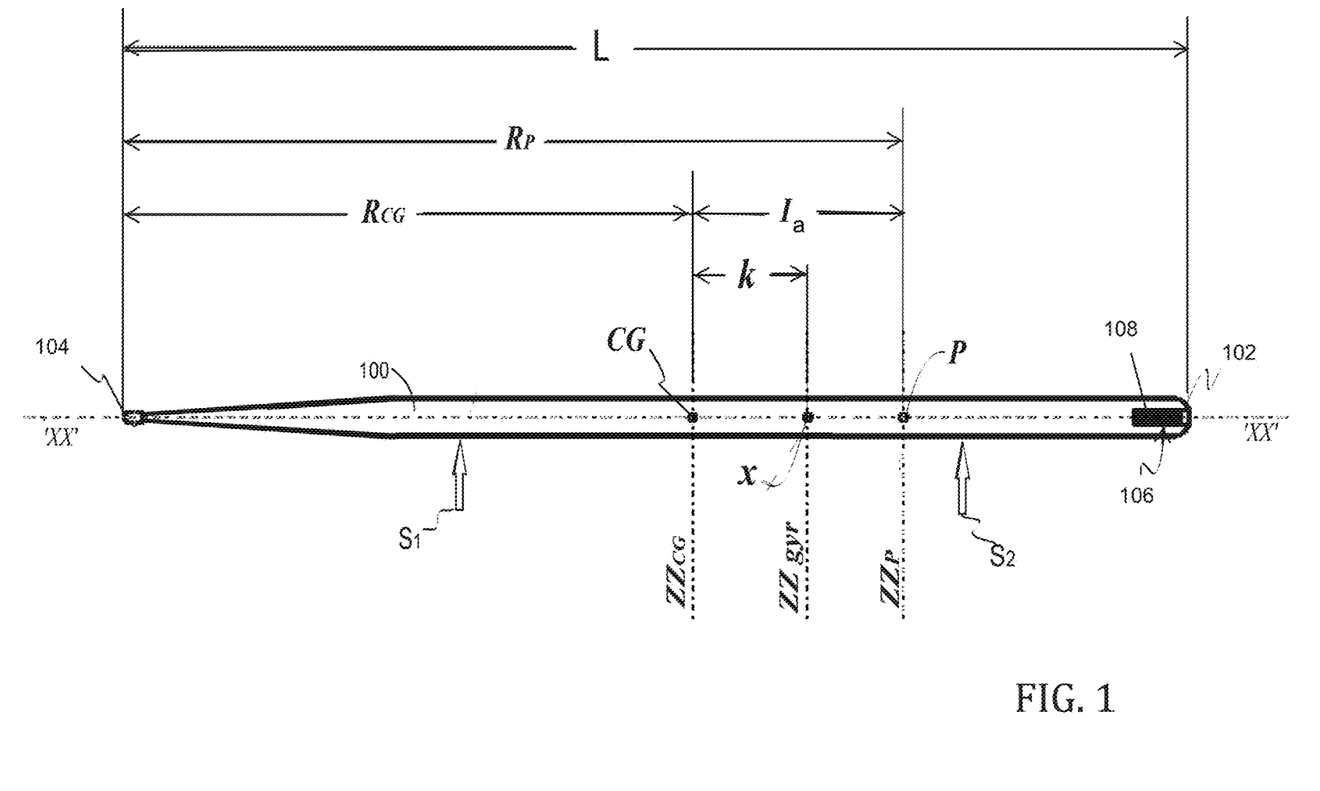
FIG. 1 is a side view of a drumstick.
Figures 2, 3, 4:
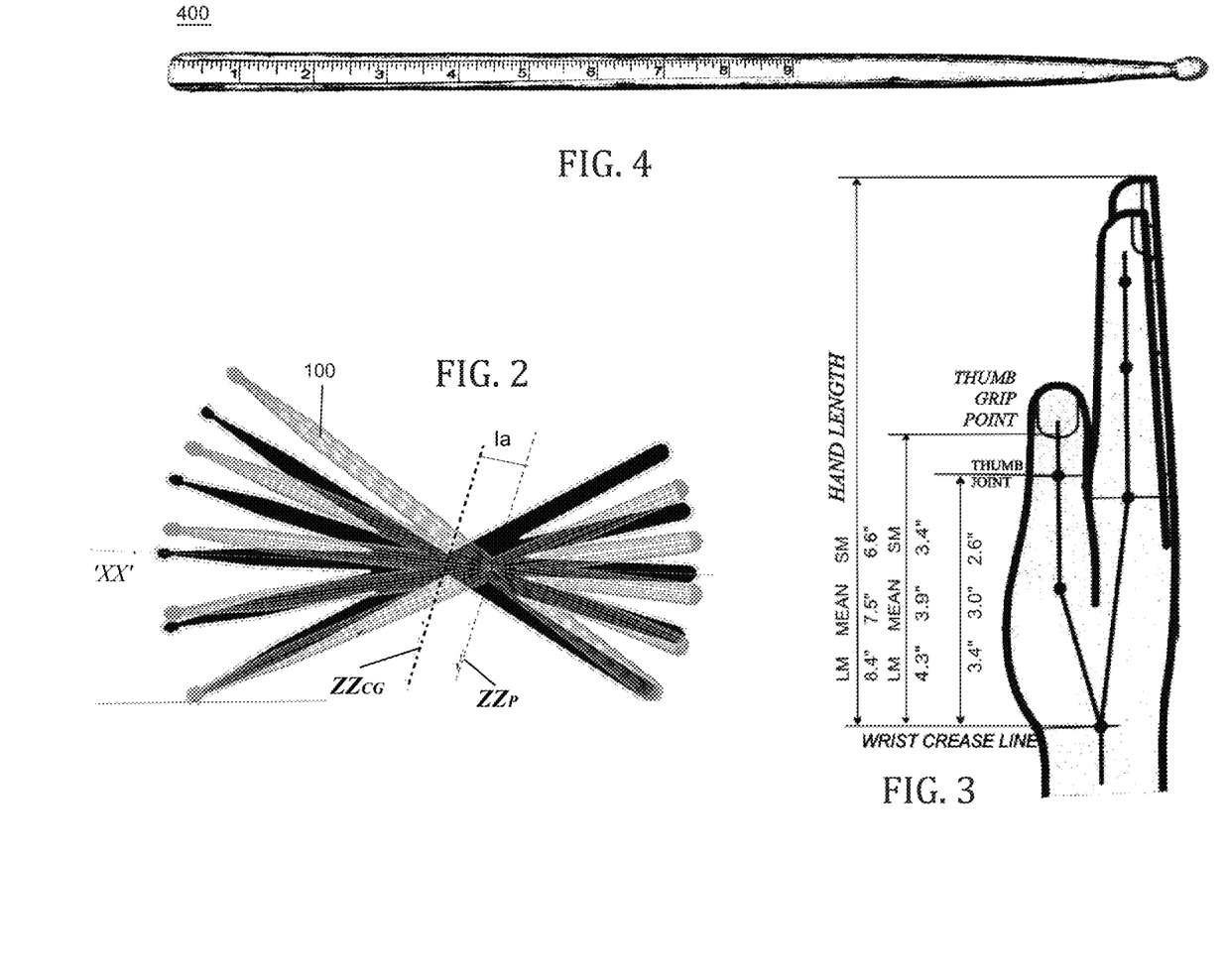
FIG. 2 is a diagram of a transition of two different rotational axes, which demonstrates the principle of wobble.
FIG. 3 is a conventional diagram representing hand size for a male and a female.
FIG. 4 is a grip stick scale that may be used to determine the grip position of a drummer on a drumstick.

Referring first to FIGS. 1 and 2, the operation of a drumstick is explained with reference to a wood or synthetic drumstick 100 balanced according to the teachings herein. In drumstick (also called a stick) 100, the handle end of stick 100 that is griped is referred to as a butt end 102, while the end of stick 100 that strikes a drum is referred to as a tip or striking end 104. Stick 100 includes a balance adjustment hole 106 that houses a weight element 108 as described in additional detail hereinafter.

For the purposes of the description herein, an unbalanced drumstick is defined as a drumstick or a drum mallet that has not been modified to achieve a repositioned center of gravity. Similarly, a balanced drumstick is defined as a drumstick or drum mallet that has been modified to achieve a repositioned center of gravity. A custom drumstick is defined as a balanced drumstick for a specific user or performance result. References to a drumstick or stick herein encompasses a drum mallet.

Weight element 108 moves the existing center of gravity CG of an unbalanced drumstick to a new center of gravity x as described in additional detail hereinafter. The center of gravity of stick 100, both before and after modification, may be measured by two scales S1 and S2 that are described in additional detail with respect to FIGS. 7-10. Stick 100 has a total length L from butt end 102 to tip end 104 with a central longitudinal axis XX.

For the purposes of this specification, a drummer will include anyone playing drums, tom-toms, cymbals, cowbells, bongos, marimbas, or any other percussion instrument using a drumstick. A drumstick described herein thus may include a drumstick having the shape of FIG. 1 or other known shapes. A drumstick may be formed of wood or synthetic materials, with the synthetic materials including, for example, metal, plastic and/or resin, with or without reinforcement by cloth or fibers.

For the purposes of this specification, balance point, center of mass and center of gravity may be equivalent terms. Further, and for ease of description, the units of weight and mass may be used interchangeably. Although the mass center and center of gravity of a particular drumstick may not be the same in actuality due to defects or variations in the drumstick along its length and width, such differences are not considered in this description since the variation would be small. Thus, the mass center and the center of gravity are treated as occurring at the same point.

Throughout this specification, certain theories are presented to describe actual observations of operation of drumsticks, before and after changes in the center of gravity of the drumsticks. The present teachings are not to be bound by any theory.

In a down stroke, a drummer's grip point P of stick 100 defines the primary rotation axis, which is perpendicular axis of rotation $ZZ_P$ in FIG. 1. Grip point P is usually defined as a distance from butt end 102. Rebounding and turning up, center of gravity CG defines the primary rotation axis, which is perpendicular axis of rotation $ZZ_{CG}$ in FIG. 1. With further reference to FIG. 2, it is believed that this change in rotational axis introduces wobble to stick 100. Wobble is seen at faster tempos and is felt far before maximum speed is reached. Wobble represents a conflict between two distinctly different rotational axes resulting in apparent rotational instability indicating that the inertial axes are not aligned with the principal axes. Wobble is unbalanced rotation of a drumstick, producing undesirable characteristics in the "feel" a drummer perceives. Those characteristics—centrifugal force, stick shock and vibrations—may result in a loss of speed, power and control of a drumstick. To stay in control of the drumstick, it is common for a drummer's hands to become fatigued and his/her grip to become tighter. Pain often develops after playing for an extended period of time that sometimes persists so as to cause a chronic condition.

The axis of rotation is the perpendicular instantaneous axis about which the drumstick rotates. There are three axes of rotation described herein. The first two—axis $ZZ_{CG}$ and axis $ZZ_P$—are described above. Referring again to FIG. 1, the third axis of rotation is axis $ZZ_{gyr}$. It is located between axes $ZZ_{CG}$ and $ZZ_P$ at point x, which is the new center of gravity of stick 100 when balanced. The location of point x is described below.

Axis $ZZ_{gyr}$ may also be referred to as the principal moment (or primary axis) of inertia or the radius of gyration. That is, a mass moment of inertia is a rotational counterpart of mass and is a measure of mass distribution about an axis. For a particle, its value is the product of mass M times the square of the distance r from the axis to the particle, $M*r^2$. For a rigid body, its value is an integral, $\int r^2 \, dM$. Since the mass moment of inertia is calculated with respect to an arbitrarily specified axis, its value depends upon the chosen axis. There are corresponding principal moments of inertia for each axis of drumstick 100. Where an axis of rotation is not coincident with a principal axis, drumstick 100 is unbalanced.

Referring again to FIG. 2, the magnitude of the imbalance is a couple and a function between axes $ZZ_{CG}$ and $ZZ_P$. A couple is a system of the two parallel forces along axes $ZZ_{CG}$ and $ZZ_P$, equal in magnitude and acting in opposite directions. A couple causes a moment or torque proportional to the distance between the parallel forces and is called the couple arm Ia.

Balancing stick 100 by aligning a principal inertia axis with an axis of rotation through the addition or removal of material, such as weight element 108, can result in significant quality and performance improvements. Such alignment reduces centrifugal forces, minimizing vibration, stress and associated wear on the body and drumstick. Alignment may be used to improve the feel of drumstick pairs. Regarding feel, "research has indicated that the perception of various properties of occluded objects by dynamic touch is a function of the object's resistances to angular rotation." Pagano, C. C., "Implications of Dynamic Touch for Human Factors/Ergonomics: Contributions from Ecological Psychology—Dynamic Touch in Varying Media and for Proprioception," Proceedings of the Human Factors and Ergonomics Society 48th Annual Meeting, pp. 1321-1325 (September 2004). This dynamic touch function of the grip of the drumstick correlates this specific "feel" relationship between drummer and drumsticks. What drummers call the "feel" is the dynamic touch perception of the drumstick's properties, relative to the grip and actions of the drumstick's rotation. This touch perception is sensitive and can sense less than a 1% variant in balance between sticks.

Thus, balancing drumsticks desirably aligns axes as described and removes variations between sticks of drumstick pairs.

In the book "Understanding Drum Techniques," the present inventor describes that the drumstick is to be considered as a lever, revolving about a fixed point called a fulcrum.

Hughlett, D., "Understanding Drum Techniques," p. 4 (1985). This fulcrum is the grip point about which the drumstick rotates with respect to the hand. In playing a percussion instrument, the drumstick is rotated about an axis in space established by the drummer generally lateral to the axis of the drumstick. To play properly, a drummer should establish a stable fulcrum or grip point. The drumstick remains at the fulcrum and is rotated by movement of the hand to strike and play the percussion instrument.

Grip position or point P defines primary perpendicular axis of rotation $ZZ_P$ of the down (striking) turn of drumstick 100. Grip point P is used to determine and locate the radius of gyration, which becomes the new anticipated center of gravity location x for each respective drumstick 100 based upon the constant radius of gyration $ZZ_{gyr}$ for a particular grip point P. Grip point P varies on drumstick 100 based on hand size, technique style and orientation.

Hand size is relevant as shown with reference to FIG. 3. FIG. 3 describes the variation in hand size for adult men, showing measurements for the largest male hands (LM), the smallest male hands (SM) and the mean values. (Developed from hand data in drawing 42 of Tilley, A. et al., "The Measure of Man and Woman: Human Factors in Design," (Wiley 2001)). FIG. 3 demonstrates that there is about a 25% difference in the length of the hands of adult men. Women also have a range of hand sizes. FIG. 3 demonstrates that even two people using the same technique style and orientation may grip drumstick 100 at a different grip point P.

A grip scale 400 as shown in FIG. 4 may be used as an aid to define the drummer's grip position P from butt end 102 on stick 100. More specifically, grip scale 400 may be used to measure the distance from butt end 102 to the fulcrum point (grip point P). The measured position on scale 400 would be grip point P for drumstick 100. The fulcrum point (and hence radius of gyration $ZZ_{gyr}$) for various technique styles is shown in the diagrams of FIGS. 5A-5F. In diagrams of FIGS. 5A-5F, axis of rotation $ZZ_{CG}$ is also shown. Other techniques or tools other than grip scale 400 may be used to obtain a measurement of grip point P for a particular drummer.

Different schools evolved a number of techniques for gripping drumstick 100 as a result of different needs and preferences for drumstick characteristics. These include technique style and orientation. In an overhand matched grip, both hands support a stick with the same grip as the dominant hand. In a traditional (open or left hand) grip, the weaker hand supports the drumstick between the base of the index finger and thumb. The different techniques use drumsticks as first and third class levers.

In FIGS. 5A-5D, dominant hand (RH) technique styles are first described.

Figures 5A, 5B, 5C, 5D, 5E, 5F:
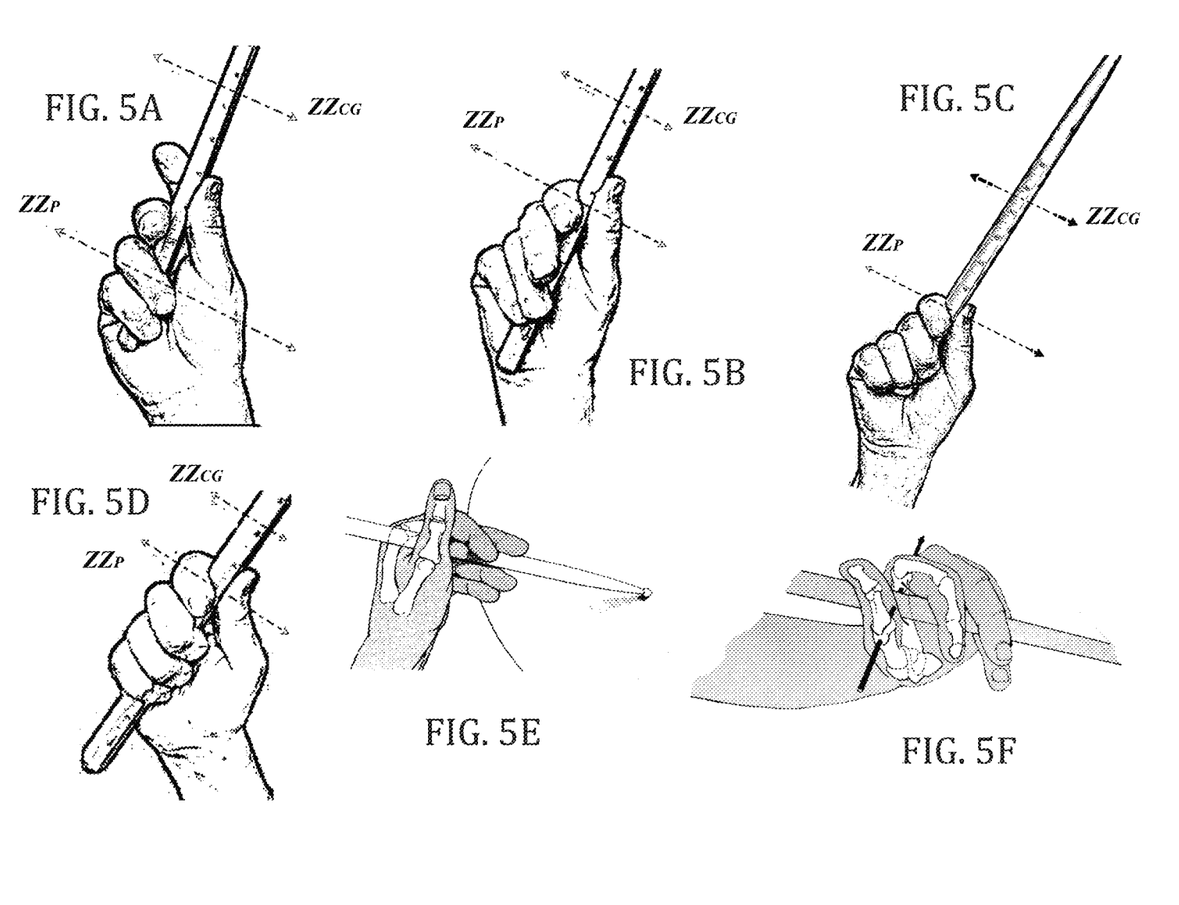
FIGS. 5A-5F include a series of diagrams illustrating the variances in grip position for stick grip styles.

In FIG. 5A, the Moeller technique is shown. It is believed that Moeller described the method after observing Civil War drummers in the 19th century. The technique style consists of pressing or "gripping" the drumstick predominately with the little finger. The other fingers are then curled gently around the drumstick without pressing tightly. With this approach, the fulcrum is situated at the back of the hand as shown by axis $ZZ_P$. A variation in this technique uses the index and/or middle fingers to grip the drumstick. The variation moves grip point P on drumstick 100 further from butt end 102 than the conventional Moeller technique shown. In this technique, drumstick 100 works as a third class lever.

A Corp (also called Marching) technique that grips the right drumstick with the little finger was normally associated with "ancient-style" drumming. This is also known as a pre-1920s grip normally taught to military drummers going back to the American Revolution. This Corps technique has progressed and continues to be used today as a third class lever.

Another grip is described in U.S. Pat. No. 1,484,777. Therein, "sticks must be grasped lightly near the balance between the thumb and forefinger [for] pivotal movement." The grip is desirably at a point ⅓ (33%) from butt end 102 of drumstick 100. (See also Harr, H. W., "Drum Method: For Band and Orchestra (M.M. Cole Publishing 2006)).

In the French grip, drumsticks are moved mainly by the fingers as first class levers. Drumsticks are moved mainly by the wrists in the German grip as first class levers. The American grip is partway between the French and German grips, using both wrists and fingers to move each drumstick as a first class lever.

The Adler technique shown in FIG. 5B establishes an A-line to a strong fulcrum point formed by the thumb pad and a first joint of the index finger. In this way, muscles purely in the hand are used to grip the drumstick to work as a first class lever.

FIG. 5C illustrates the Timbale technique The Timbale technique uses the middle and ring fingers to grip a drumstick with the butt end in the middle of the palm. The drumstick works as a third class lever.

Some hard hitting rockers use their drumstick like clubs or hammers. This is also called a fingers grip. (See FIG. 5D).

In contrast to these dominant hand (RH) technique styles, the traditional (LH) grip is shown in FIGS. 5E and 5F. The traditional grip was introduced with the first military drummers of the 19th century. Then, a marching drum was held with an over-shoulder sling and hung along the side of the drummer's leg. This position made the overhand match grip impractical as the elbow for the arm closer to the drum would have to be at shoulder height.

Next discussed is a method of determining the new center of gravity x of a drumstick that can be used to produce one balanced drumstick 100 or balanced drumstick pairs. The calculations below are described with reference to the variables identified in FIG. 1. In general, once a particular radius of gyration is calculated, the dynamic equations for ridge body rotation are used to correlate to the new center of gravity location based upon that radius. The new center of gravity is adjusted, e.g., by the addition of weight 108 into a hole 106 in butt end 102 of drumstick 100. Dynamically balanced drumsticks result, each being balanced to the same radius of gyration. Pairs of drumsticks can be matched by weight for optimum drumstick pairs.

Broadly, the steps of the method include finding two axes $ZZ_{CG}$ and $ZZ_P$ in the same plane perpendicular to the longitudinal axis XX of a drumstick. Axis $ZZ_{CG}$ is defined by existing center of gravity CG of the drumstick. The drummer defines the particular grip point or position P of a model of the drumstick to be balanced corrected (e.g., grip stick 400). Axis $ZZ_P$ is defined by grip point P. The difference between the two moments of inertia associated with axes $ZZ_{CG}$ and $ZZ_P$, respectively, is a moment arm that can be used to calculate a distance from existing center of gravity CG or grip point P that will result in new center of gravity x. Once new center of gravity x is found, it may be used to generate a weight element 108 to change the location of the existing center of gravity CG to the location of the new center of gravity x.

Additional details of these steps may be had by reference to FIGS. 7-10. FIGS. 7-10 illustrate balanced drumstick system 700, also called drumstick balancing system 700, comprising a first scale $S_1$, a second scale $S_2$, a computer system 702, an actuator 704, a cutting device 706, a distance locator 800 and weight element 108 configured to balance a conventional drumstick (i.e., drumstick 100 before the addition of weight element 108).

First scale $S_1$ and second scale $S_2$ measure weight (or mass) M of drumstick 100. First scale $S_1$ comprises a weight-measurement scale configured to measure a portion of the weight M of drumstick 100 at a first location along the length L of drumstick 100 and generate a signal 900 representing the weight measurement. Second scale $S_2$ comprises a weight-measurement scale configured to measure a portion of the weight M of drumstick 100 at a second location along the length L of drumstick 100 and generate a signal 902 representing the weight measurement. The signals 900 and 902 from first scale $S_1$ and second scale $S_2$ are inputted to computer system 702.

Figure 7:
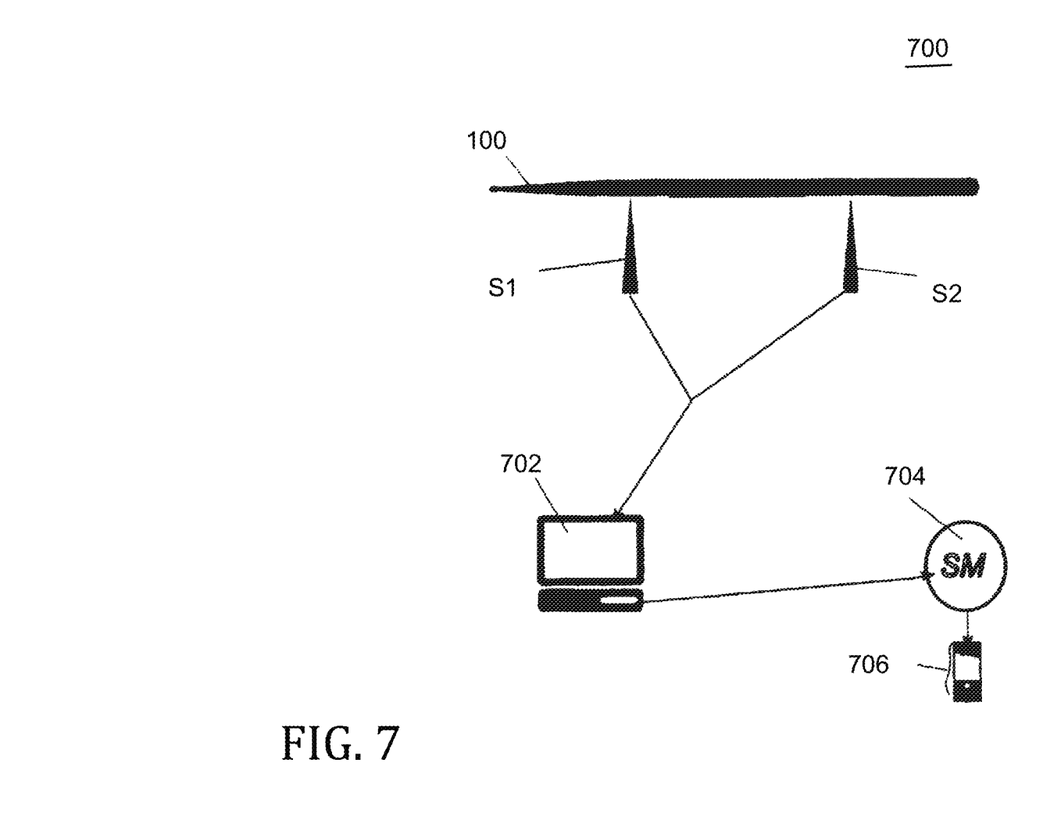
FIG. 7 is a schematic view of an apparatus for producing balanced drumstick pairs according to one implementation of the teachings herein.
Figure 8:
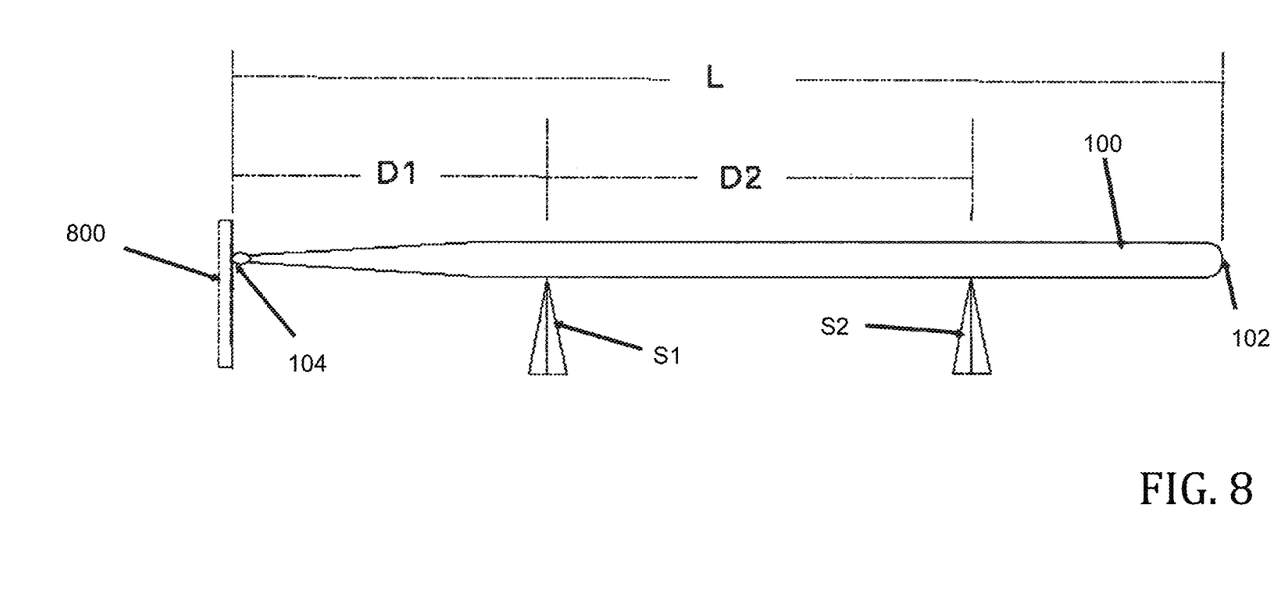
FIG. 8 is a simplified side view of the drumstick of FIG. 1 illustrating a mounting position with respect to the apparatus of FIG. 7.

Signals 900 and 902 may be used to find a location of existing center of gravity CG and a total weight M. More specifically, as shown in FIGS. 7 and 8, drumstick 100 is placed to rest on defined points of first scale $S_1$ and second scale $S_2$ such that striking end 104 of drumstick 100 is located nearest to first scale $S_1$. Length L of drumstick 100 from butt or handle end 102 to tip or striking end 104 is measured. The distance from striking end 104 to the location on drumstick 100 that bears weight on first scale $S_1$, defined as D1, is measured. The distance from the location on drumstick 100 that bears weight on first scale $S_1$ to the location on drumstick 100 that bears weight on second scale $S_2$, defined as D2, is measured. Length L and distances D1 and D2 are inputted to computer system 702.

FIG. 8 illustrates an example embodiment of balanced drumstick system 700 wherein striking end 104 of drumstick 100 is placed against a distance locator 800 and the locations of first scale $S_1$ and second scale $S_2$ are in a fixed geometric arrangement relative to each other and also relative to distance locator 800. Distance locator 800 comprises a vertical surface against which striking end 104 of drumstick 100 is placed. The fixed geometric arrangement of first scale $S_1$, second scale $S_2$ and distance locator 800 relative to each other results in distances D1 and D2 that are constant for any length L of drumstick 100. The embodiment shown in FIG. 8, when applied to a plurality of drumsticks comprising two or more drumsticks 100, allows distances D1 and D2 to be inputted to computer system 702 once. In other embodiments, distance locator 800 may be omitted.

Figure 9:
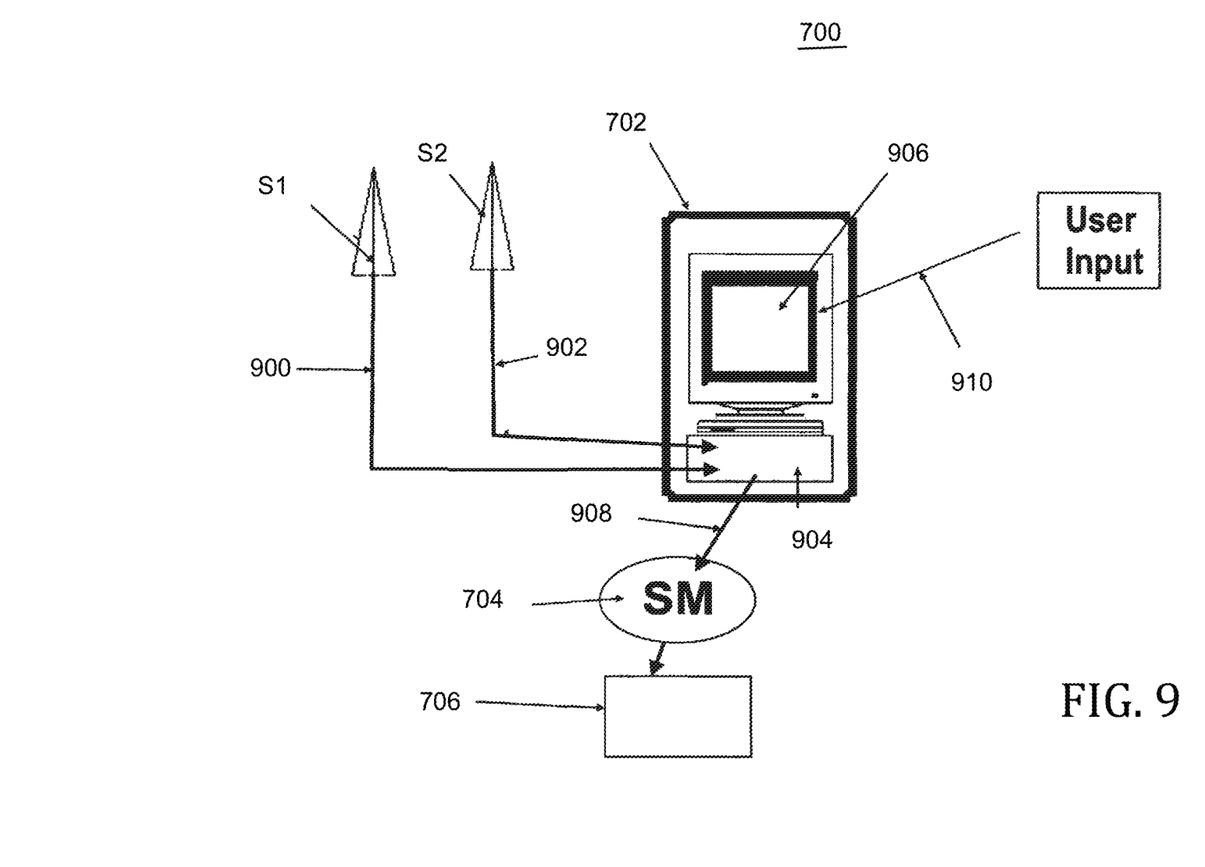
FIG. 9 is a further schematic view of the apparatus of FIG. 7.

As shown in FIGS. 7 and 9, computer system 702 includes a microprocessor 904 and a user interface 906. Microprocessor 904 is configured to generate control signals 908 based upon user input 910 through the user interface 906 and weight signals 900 and 902 from first scale $S_1$ and second scale S2. User input through user interface 906 includes, among other variables, measured distances D1 and D2 and measured length L. Microprocessor 904 performs its calculations according to computer code stored in memory of computer system 900 in one implementation. In others, some or all the calculations may be performed using different devices instead of or in addition to microprocessor 904, such as hardware components (ASICs, etc.) Microprocessor 904 may represent one processor or several processors.

Microprocessor 904 calculates the weight M of drumstick 100 by summing weight inputs 900 and 902 from first scale $S_1$ and second scale $S_2$. Microprocessor 904 locates, by calculation, an original longitudinal center of gravity CG of drumstick 100 using distances D1 and D2, length L, weight inputs 900 and 902 from first scale $S_1$ and second scale $S_2$, respectively, and the calculated weight M of drumstick 100. Using these inputs, and others described below, a desired new longitudinal center of gravity x of drumstick 100 may be calculated by microprocessor 904.

First, grip point or fulcrum P from butt end 102 may be measured using grip scale 400 or other techniques and inputted to computer system 702. As mentioned above, a moment of inertia can generally be represented by $M*r^2$ where M is a mass and r is a distance (e.g., a radius) from the axis to a point. The difference between two moments of inertia is the couple moment (or moment arm) I of inertia, where radius of gyration $ZZ_{gyr}$ defines the third, intermediate axis and new target center of gravity location x. Using Newton's second law of rotation involves the assumption that the axis about which the rotation is taking place is a principal axis in two-dimensional space. Since most common rotational problems involve the rotation of an object about a symmetrical axis, the use of this equation is usually straightforward, because axes of symmetry are examples of principle axes. A principal axis may be simply defined as one about which no net torque is needed to maintain rotation at a constant angular velocity. The moment about any other axis may be determined by the parallel axis theorem whereby: $I=\frac{1}{3}Mr^2$.

Given length L of drumstick 100 between butt end 102 and tip end 104 and the location of grip point P from butt end 102, the distance from grip point P to tip end 104, which is also a radius $R_P$ of the lever arm about axis of rotation $ZZ_P$, may be calculated. Namely, radius $R_P$ is equal to L−P. Knowing the location of existing center of gravity CG, the distance from center of gravity CG to tip end 104 may be calculated. This distance is a radius $R_{CG}$ of the lever arm about axis of rotation $ZZ_{CG}$. The moment of inertia $I_P$ about grip point P is equal to $M*R_P^2*\frac{1}{3}$. The moment of inertia $I_{CG}$ about center of gravity CG is equal to $M*R_{CG}^2*\frac{1}{3}$. Couple arm Ia between the moments of inertia is equal to $I_P - I_{CG}$.

The value of couple arm Ia is also equal to $M*k^2$, where k may be considered to be the radius of gyration and is the distance between existing center of gravity CG and the unknown location new center of gravity x. Accordingly, $Ia=M*k^2$ may be solved for radius k according to $$k = \sqrt{\frac{Ia}{M}}.$$

New center of gravity x can be determined from either tip end 102 or butt end 104 using other existing variables. For example, new center of gravity x could be defined adding the radii $R_{CG}+k$.

In this way, the drummer's grip point location that results in different axes of rotation relative down strokes and up strokes may be used to locate a new position of the center of gravity along a length of a drumstick. Addition of weight element 108 (or the removal of weight from drumstick 100 if needed) may be used to move the center of gravity to the new position to thereby minimize wobbling resulting from the differing axes, and a single or plurality of drumsticks weighted and balanced to the same radius of gyration may be produced.

Figure 10:
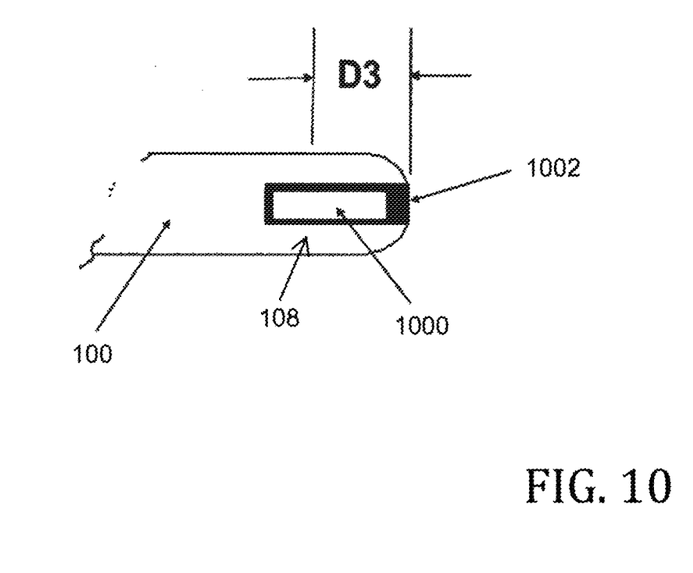
FIG. 10 is a close-up cross-sectional view of the butt end of a drumstick balanced in accordance with the teachings herein.

As illustrated in FIG. 10, weight element 108, when affixed to butt end 102 of drumstick 100, permanently repositions the longitudinal center of gravity of drumstick 100 from the original calculated location CG to the desired new location x. Weight element 108 comprises a weight 1000 configured of metal material that is uniform in cross-sectional area and uniform in density that may be encapsulated with an encapsulating material 1002. The uniform cross-sectional area and uniform density of the material for weight 1000 are inputted to computer system 702 through user interface 906. A center of gravity location for weight element 108 at a distance D3 from butt end 102 of drumstick 100 is specified and inputted to computer system 702 through user interface 906. A weight allowance for the method of fixation of weight 1000 to drumstick 100 (e.g., encapsulating material 1002) and a location for the fixation method weight allowance are specified and inputted to computer 702 through user interface 906, wherein the location for the fixation method weight allowance is distance D3 from butt end 102.

In one embodiment of balanced drumstick system 700, the metal material from which weight element 108 is configured comprises lead. In other embodiments, the metal material may comprise another metal or a similar material that is substantially higher in density than wood.

Microprocessor 904 calculates the required weight of weight element 108 to reposition the longitudinal center of gravity of drumstick 100 from the calculated original location CG to the specified new desired location x based upon user inputs. Microprocessor 904 calculates the required length of weight 1000 based upon the calculated required weight of weight element 108, the weight allowance and the inputted uniform cross-sectional area and uniform density of the metal material used to configure weight element 108. Microprocessor 904 generates output control signals based upon the calculated length of weight element 108 and configured to control actuator 704.

Actuator 704 is configured to receive control signals 908 generated by microprocessor 904 and to operate cutting device 706 so as to cut weight 1000 based upon the control signals 908. Actuator 704 comprises a device configured to grip or hold metal material for weight 1000 and to move the metal material for weight 1000 into position for cutting to the required length calculated by microprocessor 904. After the metal material for weight 1000 is positioned, actuator 704 actuates cutting device 706 to cut the material to the required length to create weight element 10. Cutting device 706 comprises one of a knife, saw, scissors, grinder and torch configured to cut material for weight 1000 to the required length.

In an example embodiment of balanced drumstick system 700, cutting device 706 comprises a movable clamping or holding structure controllably driven by a stepper motor as actuator 704.

Weight 1000 is affixed to butt end 102 of drumstick 100 by a method of permanent attachment, wherein weight 1000 moves in synchronization with movement of drumstick 100 and wherein there is no relative movement between weight 1000 and drumstick 100. The method of attachment of weight 1000 to drumstick 100 comprises one or more of an adhesive, a cap and a plug, wherein weight 1000 is encapsulated within the one or more of an adhesive, a cap and a plug as encapsulating material 1002 such that there is no direct contact between the surfaces of weight 1000 and drumstick 100.

Drumstick 100 balanced to a new longitudinal center of gravity x by the teachings herein has a repositioned longitudinal center of gravity within 0.25% of the length of drumstick 1000 from the new longitudinal center of gravity.

Figure 6:
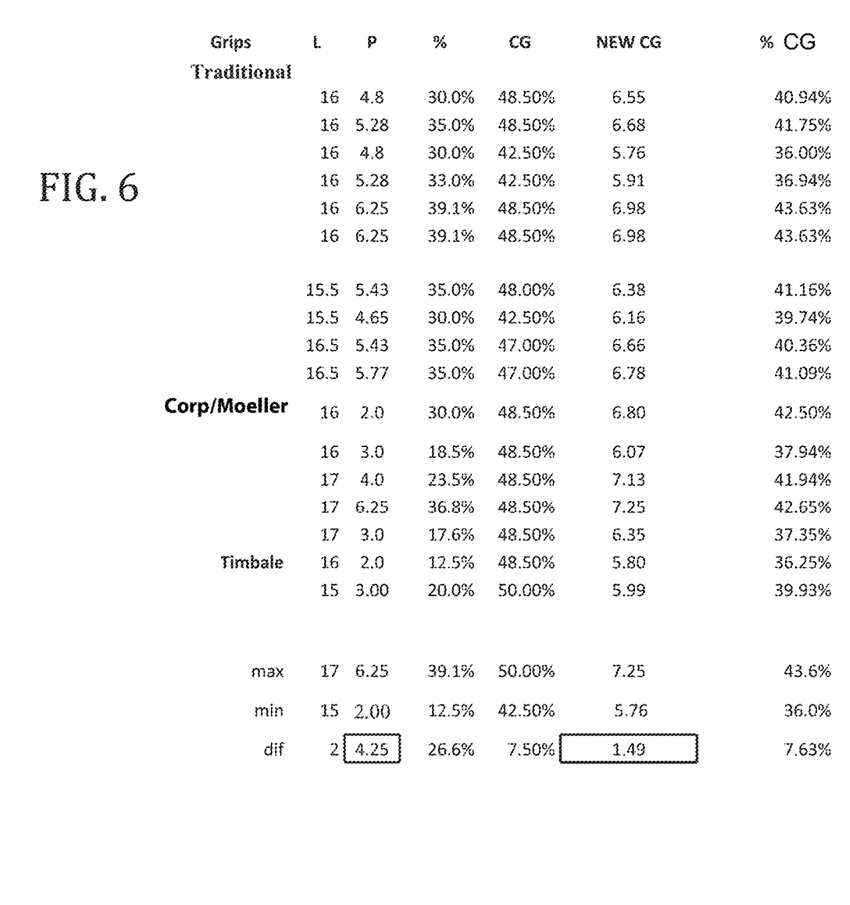
FIG. 6 is a table summarizing a grip point radius of gyration.

The test results of FIG. 6 demonstrate the results of balancing a plurality of drumsticks according to the techniques described herein. Drumsticks having different lengths L between 15 and 17 inches and a constant mass of 56 grams were held in three different grips—traditional, Corp (or Moeller) and Timbale—as described above to determine grip point P (in inches) of each drumstick. The distance to grip point P relative to the butt end of each drumstick is represented by a percentage (%) of length L in FIG. 6. As can be seen in FIG. 6, for the same grip style, the variation in grip point P due to hand size is significant. The locations CG of existing center of gravity relative to the butt ends of each drumstick range between 42.5 and 50.0% of length L.

A new location of the center of gravity for each drumstick is shown in distance (New CG) from the butt end (in inches) and in percentage of distance (% CG) from the butt end. The locations (New CG) of the new centers of gravity relative to the butt ends of each drumstick range between 36.0 and 43.6% of length L. Due to the relatively large variance in hand size, the grip point P (difference of about 4.5") is a direct controlling parameter in the difference of 1.5" in the position CG of the radius of gyration (i.e., the new center of gravity).

While computer system 700 is used to calculate the existing centers of gravity, calculate the new centers of gravity and form weight 1000 for weight element 108, this is not necessary. In some embodiments of the invention, different systems could be used for each of these major functions, with or without manual inputs from one system to another system. In other cases, portions of these major functions may be performed manually. For example, upon output of the desired length of weight material needed for weight element 108, actuator 704 and cutter 706 may be operated manually instead of under the control of microprocessor 702.

In some implementations, it may be desirable to start the process by using a group of similar drumsticks so as to determine an average weight and average position of center of gravity. Using these averages, and average values for grip point P based on grip style/model, a new constant radius of gyration x may be calculated. This value may be used for each of the drumsticks as a correlated target new center of gravity location for the group of drumsticks. In this case, a weight element 108 may be calculated for each drumstick using the correlated target. Ideally, this single weight would make a correction in the plane of the mass center sufficient to shift the existing gravity center onto the new anticipated center of gravity location. The radius of gyration is thus the controlling parameter in accordance with the dynamics of a rigid body system as defined by the equations of motion, which are derived using either Newton's laws of motion or Lagrangian mechanics.

According to the teachings herein, re-distribution of the drumstick mass may be performed so as to better align the central principle inertia axis with the axis of rotation. The strategic addition or removal of weight redistributes the mass, altering the mass properties to better align the mass center and the central principal axis with the axis of rotation. The principal moments of inertia of rotation are used to determine a radius of gyration for each particular grip model. Then, the center of gravity of the drumstick is desirably positioned at or around the point of radius of gyration along the drumstick.

One may first correlate a specific relationship between a conventional drumstick center of gravity and the particular grip position to obtain a radius of gyration. Using the radius of gyration as the controlling parameter thereafter balances other drumsticks in accordance with that radius for a particular grip position on the drumstick, model, preference or a particular plurality of the drumsticks.

When the drumstick comprises wood, the natural inconsistencies in the material make it desirable to individually weigh and find the center of gravity, then balance the drumstick to a common new center of gravity destination for every drumstick of a particular model. Then, the drumsticks so balanced may be weighed again to match like weights to generate balanced pairs.

According to the teachings herein, one or more drumsticks may be balanced to a single, selected radius of gyration. Balanced drumsticks provide optimum performance, control and handling characteristics. They improve a drummer's playing as the drumsticks may be custom balanced for a user's techniques, hand size and grip styles. The balance position of preference may be tweaked given the knowledge of the radius of gyration.

Adjusting the center of gravity as described may result in improvements in speed, power, center of percussion and preferred sweet spot.

In use, drumsticks made as described herein have a center of gravity at or about the radius of gyration about which the drummer grips and rotates the drumsticks to strike the instrument. The resulting balanced rotation of the drumstick, results in a more solid better "feel" to the drummer. The radius of gyration, at or about the center of balance to the grip, can result in less centrifugal force tending to pull the drumstick axially out of the drummer's hand as the drummer rotates the drumstick to strike the instrument as hereinbefore described. A lesser (lighter or looser) grip is therefore required to hold on to the drumstick and provide a more consistent turn.

Gripping with fingers and turning the wrist can result in tendonitis and carpel tunnel syndrome. User friendly, the drumsticks balanced as described herein with a new anticipated center of gravity location, uses grip position and radius of gyration as the controlling parameters, to reduce the needed grip.

The teachings described herein desirably result in sets of drumsticks with a common, repositioned longitudinal center of gravity. The drumsticks of the plurality are substantially equal in length and shape, but have unequal weights and original longitudinal centers of gravity due to density variations inherent to wood material.

The alteration of the mass properties of a balanced drumstick improves the alignment of the axis of rotation with the mass center and/or the central principal axis such that the moment of inertia and energy of rotation would be relatively unchanged during operation, providing stabilization of turns.

In the example embodiment illustrated, drumstick balancing system 700 facilitates repositioning a longitudinal center of gravity of each of the drumsticks within 0.25% of the length of the drumstick from the common new specified longitudinal center of gravity for the plurality. Balanced drumstick system 700 may automate the repositioning of the longitudinal center of gravity of drumsticks to increase accuracy and to decrease time to create sets of custom drumsticks.

The teachings herein can result in a plurality of drumsticks of substantially equal length and shape, each drumstick including a handle end with a weight element affixed thereto, a striking end, and an original longitudinal center of gravity in an absence of the weight element. For each one of the drumsticks, a longitudinal center of gravity including the weight element is located nearer to the handle end than the original longitudinal center of gravity, and the weight element has a weight selected to reposition the original longitudinal center of gravity of the drumstick toward the handle end to a common target longitudinal center of gravity. For each of the drumsticks, the weight element comprises a material encapsulated within the handle end such that there is no direct contact between surfaces of the material and the drumstick. Also, the weight element is centered at a target position within the handle end that is common to each one of the drumsticks.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope of the disclosure and the appended claims.

What is claimed is:

1. A method, comprising:
   receiving, at a processor, a first weight from a first weight-measurement scale and a second weight from a second weight-measurement scale, a drumstick simultaneously bearing weight on the first weight-measurement scale and the second weight-measurement scale;
   calculating a position of an existing center of gravity of a drumstick along a length of the drumstick using the first weight and the second weight, the position defining a first axis of rotation perpendicular to a central axis of the drumstick;
   generating, using the first axis of rotation and a second axis of rotation perpendicular to the central axis of the drumstick, a radius of gyration for the drumstick, the radius of gyration defining a third axis of rotation perpendicular to the central axis of the drumstick and the second axis located at a grip point along the length of the drumstick that is based on a grip technique of a drummer when using the drumstick; and
   calculating a weight value for a weight element that, when affixed to a handle end of the drumstick, changes the existing center of gravity of the drumstick to a desired new center of gravity that is based on the radius of gyration.

2. The method of claim 1 wherein generating the radius of gyration comprises:
   calculating a first moment of inertia of the drumstick relative to the first axis;
   calculating a second moment of inertia of the drumstick relative to the second axis;
   calculating a moment arm of inertia for a couple arm between the position of the existing center of gravity and the grip point as a difference between the first moment of inertia and the second moment of inertia; and
   using the moment arm of inertia to calculate the radius of gyration along the length of the drumstick.

3. The method of claim 2 wherein the location of the radius of gyration along the length of the drumstick is the desired new center of gravity.

4. The method of claim 2 wherein:
   calculating the first moment of inertia comprises calculating the first moment of inertia using at least one of the first weight or the second weight of the drumstick and a distance between a tip of the drumstick and the position of the existing center of gravity; and
   calculating the second moment of inertia comprises calculating the second moment of inertia using the at least one of the first weight or the second weight and a distance between the tip of the drumstick and the grip position; wherein the new center of gravity is equal to the distance between the tip of the drumstick and the position of the existing center of gravity plus the radius of gyration.

5. The method of claim 1 wherein the third axis is within the radius of gyration and between the first axis and the second axis along the length of the drumstick.

6. The method of claim 1, further comprising:
receiving the grip point, the grip point based on a hand size of the drummer measured using a grip scale.

7. The method of claim 1 wherein the desired new center of gravity is located at a point along the length of the drumstick that is coincident with the third axis.

8. The method of claim 1 wherein calculating the weight value comprises:
receiving a target position along the drumstick for a center of gravity of the weight element;
calculating a weight of the weight element required to be affixed to the handle end of the drumstick to permanently reposition the existing center of gravity to the desired new center of gravity when the weight element is at the target position.

9. The method of claim 8 wherein calculating the weight comprises:
calculating the weight based upon the desired new center of gravity, the target position along the drumstick, characteristics of a material forming the weight element, and the existing center of gravity of the drumstick.

10. The method of claim 9, further comprising:
receiving, at the processor, a density and a cross-sectional area of a metal material, the density and the cross-sectional area being uniform along a length of the metal material; and
calculating a length of the metal material required to produce the weight for the weight element.

11. The method of claim 1 wherein the drumstick bears weight simultaneously on only the first weight-measurement scale and the second weight-measurement scale such that a striking end of the drumstick is nearest to the first weight-measurement scale and contacts a distance locator at a fixed distance from a location on the drumstick that bears on the first weight-measurement scale, and calculating the position of the existing center of gravity comprises:
measuring the first weight of the drumstick bearing on the first scale;
measuring the second weight of the drumstick bearing on the second scale; and
calculating, with the first weight, the second weight, the length of the drumstick, the fixed distance and a distance between the location on the drumstick that bears on the first scale and a location on the drumstick that bears on the second scale, the position of the existing center of gravity of the drumstick.

12. An apparatus comprising:
memory; and
a processor configured to execute instructions stored in the memory to:
calculate a position of an existing center of gravity of a drumstick along a length of the drumstick, the position defining a first axis of rotation perpendicular to a central axis of the drumstick;
generate, using the first axis of rotation and a second axis of rotation perpendicular to the central axis of the drumstick, a radius of gyration for the drumstick, the radius of gyration defining third axis of rotation perpendicular to the central axis of the drumstick and the second axis located at a grip point along the length of the drumstick that is based on a grip technique of a drummer when using the drumstick; and
calculate a weight value to change the existing center of gravity to a desired new center of gravity that is based on the radius of gyration; and
a cutting device configured to cut material to form a weight element for securement to the drumstick to change the existing center of gravity to the desired new center of gravity; and
an actuator configured to move the cutting device.

13. The apparatus of claim 12, further comprising:
two weight-measurement scales, the two weight-measurement scales including a first weight-measurement scale and a second weight-measurement scale configured to measure a weight of a drumstick at a first location and a second location along the length of the drumstick, respectively, and to provide signals to the processor to calculate the position of the existing center of gravity and to calculate the weight value.

14. The apparatus of claim 12, wherein the processor is configured to generate control signals to the actuator to operate the cutting device to cut the material to form the weight element.

15. The apparatus of claim 12 wherein the processor is configured to generate the radius of gyration by:
calculating a first moment of inertia of the drumstick relative to the first axis;
calculating a second moment of inertia of the drumstick relative to the second axis;
calculating a moment arm of inertia for a couple arm between the position of the existing center of gravity and the grip point as a difference between the first moment of inertia and the second moment of inertia; and
using the moment arm of inertia to calculate the radius of gyration along the length of the drumstick.

16. The apparatus of claim 15 wherein the location of the radius of gyration along the length of the drumstick is the desired new center of gravity.

17. The apparatus of claim 15 wherein the processor is configured to:
calculate the first moment of inertia using a weight of the drumstick and a distance between a tip of the drumstick and the position of the existing center of gravity;
calculate the second moment of inertia using the weight and a distance between the tip of the drumstick and the grip position; and
calculate the desired new center of gravity by adding the distance between the tip of the drumstick and the position of the existing center of gravity to the radius of gyration.

18. The apparatus of claim 12, further comprising:
a grip scale configured to measure the grip point of the drummer.

19. The apparatus of claim 18 wherein the grip technique is one of a traditional grip or an overhand matched grip.

20. An apparatus comprising:
a surface extending in a vertical direction relative to a horizontal spacing between two weight-measurement scales comprising a first weight-measurement scale and a second weight-measurement scale, the surface located at a first distance from the first weight-measurement scale and a second distance from the second weight-measurement scale that is equal to the first distance plus the horizontal spacing between the two weight-measurement scales;

memory; and a processor configured to execute instructions stored in the memory to:

calculate a position of an existing center of gravity of a drumstick along a length of the drumstick, the position defining a first axis of rotation perpendicular to a central axis of the drumstick;

generate, using the first axis of rotation and a second axis of rotation perpendicular to the central axis of the drumstick, a radius of gyration for the drumstick, the radius of gyration defining third axis of rotation perpendicular to the central axis of the drumstick and the second axis located at a grip point along the length of the drumstick that is based on a grip technique of a drummer when using the drumstick; and calculate a weight value to change the existing center of gravity to a desired new center of gravity that is based on the radius of gyration, wherein the processor is configured to calculation the position of the existing center of gravity, calculate the desired new center of gravity, and calculate the weight value using the surface and the two weight-measurement scales.

* * * * *